US009180064B2

(12) United States Patent (10) Patent No.: US 9,180,064 B2
Prather (45) Date of Patent: Nov. 10, 2015

(54) WALKING SAFETY AID APPARATUS

(76) Inventor: Michael R. Prather, Starke, FL (US)

( * ) Notice: Subject to any disclaimer, the term of this patent is extended or adjusted under 35 U.S.C. 154(b) by 775 days.

(21) Appl. No.: 13/309,678

(22) Filed: Dec. 2, 2011

(65) Prior Publication Data

US 2013/0140781 A1 Jun. 6, 2013

(51) Int. Cl.

| A61G 5/02 | (2006.01) |
| A61H 3/04 | (2006.01) |
| A61G 5/08 | (2006.01) |
| A61G 5/10 | (2006.01) |
| A61B 5/0402 | (2006.01) |
| A61H 3/00 | (2006.01) |

(52) U.S. Cl.
CPC ............... *A61H 3/04* (2013.01); *A61B 5/0402* (2013.01); *A61B 2560/0431* (2013.01); *A61G 5/08* (2013.01); *A61G 5/10* (2013.01); *A61H 2003/002* (2013.01); *A61H 2201/0161* (2013.01); *A61H 2201/1633* (2013.01)

(58) Field of Classification Search
CPC ........................................................ A61H 3/04
USPC ......... 280/87.021, 47.38, 639, 87.03, 87.041, 280/87.05, 87.051, 47.34; 135/66, 67; 297/6
See application file for complete search history.

(56) References Cited

U.S. PATENT DOCUMENTS

| 2,362,466 A * | 11/1944 | Carter .............................. 297/6 |
| 2,374,182 A * | 4/1945 | Duke ............................... 297/6 |
| 2,759,525 A * | 8/1956 | Ries ............................... 297/6 |
| 2,796,916 A * | 6/1957 | Womble .......................... 135/67 |
| 2,866,495 A * | 12/1958 | Diehl et al. ....................... 297/6 |
| 2,996,070 A * | 8/1961 | Ries ............................... 135/67 |
| 3,436,090 A * | 4/1969 | Hebron et al. ................. 280/821 |
| 3,658,079 A * | 4/1972 | Block ............................. 135/67 |
| 3,688,789 A * | 9/1972 | Bunch ............................ 135/67 |
| 3,690,652 A * | 9/1972 | Schneider et al. ............. 482/66 |
| 3,783,886 A * | 1/1974 | Thomas .......................... 135/67 |
| 3,945,389 A * | 3/1976 | Smith ............................. 135/67 |
| 3,993,088 A * | 11/1976 | Thomas .......................... 135/67 |
| 3,993,349 A * | 11/1976 | Neufeld et al. ................... 297/6 |
| 4,046,374 A * | 9/1977 | Breyley ......................... 482/68 |
| 4,180,086 A * | 12/1979 | Thomas .......................... 135/67 |
| 4,212,493 A * | 7/1980 | Ledesky .......................... 297/6 |
| 4,277,100 A * | 7/1981 | Beougher ........................ 297/5 |
| 4,280,578 A * | 7/1981 | Perkins ......................... 180/6.5 |
| 4,298,016 A * | 11/1981 | Garelick ........................ 135/67 |
| 4,312,505 A * | 1/1982 | Engelhart ...................... 482/68 |

(Continued)

FOREIGN PATENT DOCUMENTS

JP 2000084015 3/2000

*Primary Examiner* — Brodie Follman
(74) *Attorney, Agent, or Firm* — James Ray and Assoc. I P LLC (57) ABSTRACT

A safety walker includes a pair of side members, arms and spring loaded pins engaging the arms so as to allow movement of the side members between an operative position, wherein the side members are disposed in a spaced apart generally parallel relationship with each other and a generally folded position, wherein the side members are generally juxtaposed in a generally planar relationship with and in close proximity to each other. There is also a seat that is configured for movement between a stored position wherein the seat is disposed generally parallel to a rear leg of one of the pair of the side members and a second position wherein the seat is disposed generally horizontally across a space between rear legs of the pair of the side members. The safety walker is also configured for supporting various medical devices often connected to the user.

10 Claims, 5 Drawing Sheets

(56) References Cited

U.S. PATENT DOCUMENTS

| | | | |
|---|---|---|---|
| 4,342,465 A * | 8/1982 | Stillings | 280/87.051 |
| 4,384,713 A * | 5/1983 | Deutsch et al. | 482/68 |
| 4,452,484 A * | 6/1984 | Pastor | 297/6 |
| 4,510,956 A * | 4/1985 | King | 482/68 |
| 4,518,002 A * | 5/1985 | Battiston et al. | 135/67 |
| 4,532,948 A * | 8/1985 | Burrows | 135/67 |
| 4,621,804 A * | 11/1986 | Mueller | 280/87.041 |
| 4,640,301 A * | 2/1987 | Battiston et al. | 135/67 |
| 4,748,994 A * | 6/1988 | Schultz et al. | 135/67 |
| 5,148,559 A * | 9/1992 | Morris | 5/86.1 |
| 5,188,139 A * | 2/1993 | Garelick | 135/67 |
| 5,201,333 A * | 4/1993 | Shalmon et al. | 135/67 |
| 5,271,422 A * | 12/1993 | Sorrell et al. | 135/67 |
| 5,275,187 A * | 1/1994 | Davis | 135/67 |
| 5,353,824 A * | 10/1994 | Woods et al. | 135/66 |
| 5,380,262 A * | 1/1995 | Austin | 482/68 |
| 5,411,044 A * | 5/1995 | Andolfi | 135/66 |
| 5,433,235 A * | 7/1995 | Miric et al. | 135/67 |
| 5,479,953 A * | 1/1996 | Pasulka | 135/66 |
| 5,529,425 A * | 6/1996 | Spies et al. | 403/322.4 |
| 5,706,845 A * | 1/1998 | Beyar et al. | 135/67 |
| 5,741,020 A * | 4/1998 | Harroun | 280/42 |
| 5,785,070 A * | 7/1998 | Block et al. | 135/67 |
| 5,803,103 A * | 9/1998 | Haruyama | 135/67 |
| 5,882,067 A * | 3/1999 | Carbajal et al. | 297/6 |
| 5,961,430 A * | 10/1999 | Zuckerman et al. | 482/142 |
| 5,979,476 A * | 11/1999 | Cranny | 135/67 |
| 6,003,532 A * | 12/1999 | Pi | 135/67 |
| 6,099,002 A * | 8/2000 | Uchiyama | 280/87.021 |
| 6,279,591 B1 * | 8/2001 | Obitts | 135/67 |
| 6,338,592 B1 * | 1/2002 | Chang | 403/345 |
| 6,595,530 B2 * | 7/2003 | Wood | 280/42 |
| 6,692,417 B2 * | 2/2004 | Burrell | 482/142 |
| 6,729,342 B2 * | 5/2004 | Serhan | 135/67 |
| 6,733,018 B2 | 5/2004 | Razon | |
| 6,837,503 B2 * | 1/2005 | Chen et al. | 280/87.021 |
| 6,886,575 B2 * | 5/2005 | Diamond | 135/74 |
| 7,373,942 B1 * | 5/2008 | Yeager | 135/67 |
| 7,422,025 B1 * | 9/2008 | Waldstreicher et al. | 135/71 |
| 7,494,139 B2 * | 2/2009 | Turner et al. | 280/87.021 |
| 7,497,226 B2 * | 3/2009 | Li et al. | 135/74 |
| 7,506,657 B2 * | 3/2009 | Hsiao | 135/67 |
| 7,540,527 B2 * | 6/2009 | Willis et al. | 280/642 |
| 7,568,712 B2 * | 8/2009 | Kovachi et al. | 280/87.021 |
| 7,703,465 B2 * | 4/2010 | Diamond | 135/67 |
| 7,712,477 B2 * | 5/2010 | McCarthy | 135/67 |
| 7,726,327 B2 * | 6/2010 | Battiston | 135/67 |
| 7,837,208 B2 * | 11/2010 | Willis | 280/87.021 |
| 7,950,405 B2 * | 5/2011 | Turner et al. | 135/67 |
| 8,166,988 B1 * | 5/2012 | Martin | 135/67 |
| 8,251,079 B1 * | 8/2012 | Lutz et al. | 135/67 |
| 8,292,310 B2 * | 10/2012 | Turner | 280/47.35 |
| 8,573,612 B1 * | 11/2013 | Fulk et al. | 280/87.021 |
| 8,584,689 B2 * | 11/2013 | Catton | 135/67 |
| 8,597,162 B2 * | 12/2013 | Amonette et al. | 482/66 |
| 8,720,914 B1 * | 5/2014 | Heath et al. | 280/87.021 |
| 2001/0048210 A1 * | 12/2001 | Song | 280/259 |
| 2002/0140196 A1 * | 10/2002 | Crouch et al. | 280/87.051 |
| 2003/0132613 A1 * | 7/2003 | Lin | 280/651 |
| 2004/0187901 A1 * | 9/2004 | Diamond | 135/67 |
| 2005/0005959 A1 * | 1/2005 | Diamond | 135/67 |
| 2005/0183759 A1 * | 8/2005 | Wolfe | 135/67 |
| 2007/0023073 A1 * | 2/2007 | Su | 135/67 |
| 2007/0199586 A1 * | 8/2007 | Cheng | 135/67 |
| 2007/0227570 A1 * | 10/2007 | Gale et al. | 135/67 |
| 2007/0235067 A1 * | 10/2007 | Gale et al. | 135/67 |
| 2007/0267054 A1 * | 11/2007 | Meyers et al. | 135/67 |
| 2007/0283990 A1 * | 12/2007 | Fernandez et al. | 135/67 |
| 2008/0029139 A1 | 2/2008 | Pijanowski | |
| 2008/0128008 A1 * | 6/2008 | Obitts et al. | 135/67 |
| 2008/0163913 A1 * | 7/2008 | Hsiao | 135/67 |
| 2008/0202571 A1 * | 8/2008 | Meyers et al. | 135/66 |
| 2009/0242006 A1 * | 10/2009 | Warren | 135/66 |
| 2011/0067740 A1 * | 3/2011 | Menichini | 135/67 |
| 2011/0272913 A1 * | 11/2011 | Diamond | 280/288.2 |
| 2012/0048318 A1 * | 3/2012 | Zendzian et al. | 135/66 |
| 2013/0061892 A1 * | 3/2013 | Huang | 135/67 |
| 2013/0140780 A1 * | 6/2013 | Graves et al. | 280/47.35 |
| 2013/0140781 A1 * | 6/2013 | Prather | 280/47.38 |
| 2013/0292916 A1 * | 11/2013 | Nabeta | 280/47.371 |

* cited by examiner

WALKING SAFETY AID APPARATUS

FIELD OF THE INVENTION

The present invention relates, in general, to mobility aid devices and, more particularly, this invention relates to a safety walker having side frames foldable in juxtaposed relationship with each other for storage and yet, more particularly, the instant invention relates to safety walkers having a rearwardly positioned seat that is movable between operative and storage positions.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND OF THE INVENTION

As is generally well known, safety walkers are used by many individuals with mobility impairments. Of a particular acceptance is a rear entry/egress safety walker that includes a seat member and that can be folded for ease of storage. One disadvantage of the majority of walkers presently in use is in that the seat positioned toward the front of the device, so that the user must turn around and face the back in order to use the seat. Another disadvantage is that most of the safety walkers fold front to back and require more than desired effort for the user to unlatch the safety walker for storage.

Therefore, there is a need for improved folding action of the safety walkers and a seat that can be easily configured for entry and egress of the user.

SUMMARY OF THE INVENTION

In one aspect, the invention provides a mobility aid apparatus that includes a pair of side members and means for moving the pair of side members between an operative position, wherein the side members are disposed in a spaced apart generally parallel relationship with each other and a generally folded position, wherein the side members are generally juxtaposed in a generally planar relationship with and in close proximity to each other.

In another aspect, the invention provides a mobility aid apparatus that includes a pair of side members at least releaseably fixed in a spaced apart generally parallel relationship with each other, a seat and means for moving the seat between a stored position wherein the seat is disposed generally parallel to a rear leg of one of the pair of the side members and a second position wherein the seat is disposed generally horizontally across a space between rear legs of the pair of the side members.

In yet another aspect, the invention provides mobility aid apparatus that includes a pair of side members and means for moving the pair of side members between an operative position, wherein the side members are disposed in a spaced apart generally parallel relationship with each other and a generally folded position, wherein the side members are generally juxtaposed in a generally planar relationship with and in close proximity to each other. There is also a seat and means for moving the seat between a stored position wherein the seat is disposed generally parallel to a rear leg of one of the pair of the side members and a second position wherein the seat is disposed generally horizontally across a space between rear legs of the pair of the side members.

In a further aspect, the invention provides a mobility aid apparatus that includes a pair of side members at least releaseably fixed in a spaced apart generally parallel relationship with each other, each of the side members having a top rail disposed generally horizontally during use of the apparatus, a front elongated leg extending downwardly at a first angle from one end of the top rail, a rear elongated leg extending downwardly at a second angle from one end of the top rail. There is a seat that is being supported in a generally horizontal position on the rear legs. The first angle and the second angle are so sized that the apparatus is configured to support a weight of about six hundred pounds positioned at least partially on the seat without tilting the apparatus in a rearward direction.

OBJECTS OF THE INVENTION

It is, therefore, one of the primary objects of the present invention to provide a mobility aid apparatus.

Another object of the present invention is to provide a mobility aid apparatus that includes a pair of side members and means for moving the pair of side members between an operative position, wherein the members are disposed in a spaced apart generally parallel relationship with each other and a generally folded position, wherein the side members are juxtaposed in a generally planar relationship with each other.

Yet another object of the present invention is to provide a mobility aid apparatus having a pair of side members at least releaseably fixed in a spaced apart generally parallel relationship with each other, a seat, and means for moving the seat between a stored position wherein the seat is disposed generally parallel to a rear leg of one of the pair of the side members and a second position wherein the seat is disposed generally horizontally across a space between rear legs of the pair of the side members.

A further object of the present invention is to provide a mobility aid apparatus that allows attachment of medical equipment, including at least one of a Foley bag, intravenous equipment, and cardiac monitoring equipment.

Yet a further object of the present invention is to provide mobility aid apparatus that employs wheels for ease of movement.

An additional object of the present invention is to provide mobility aid apparatus that is configured to support a weight of about six hundred pounds positioned at least partially on a rearwardly disposed seat without tilting the apparatus in a rearward direction.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE VARIOUS EMBODIMENTS OF THE INVENTION

Prior to proceeding to the more detailed description of the present invention, it should be noted that, for the sake of clarity and understanding, identical components which have identical functions have been identified with identical reference numerals throughout the several views illustrated in the drawing figures.

The present invention describes a device for aiding in or enhancing safety of a walking person (herein described as the "mobility aid apparatus" or "apparatus"), generally designated as 10, which provides means to easily change configurations of the mobility aid apparatus 10 for use and storage and further provides means to allow the walking person to rest on a movable seat positioned at the rear of the mobility aid apparatus 10.

Figure 1:
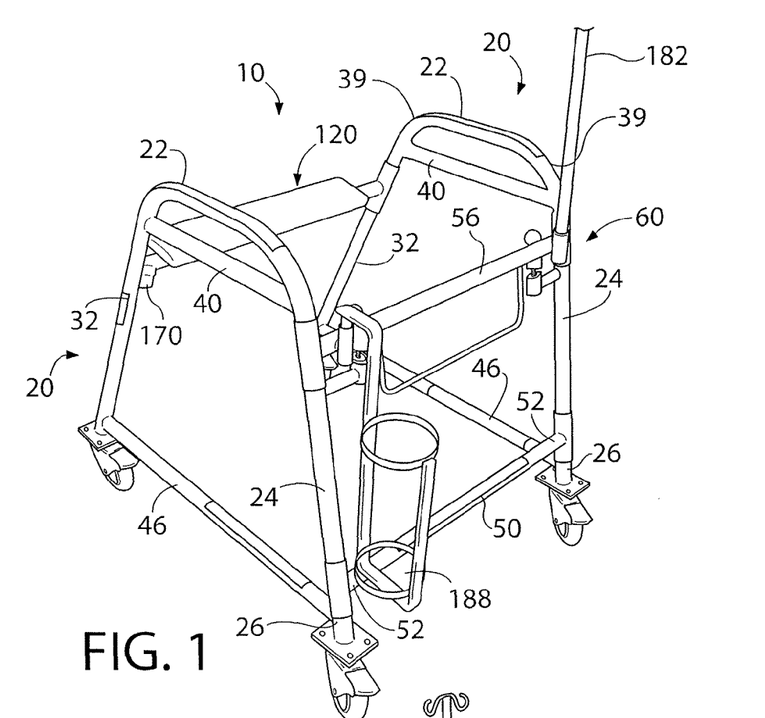
FIG. 1 illustrates a perspective view of a mobility aid apparatus.
Figure 2:
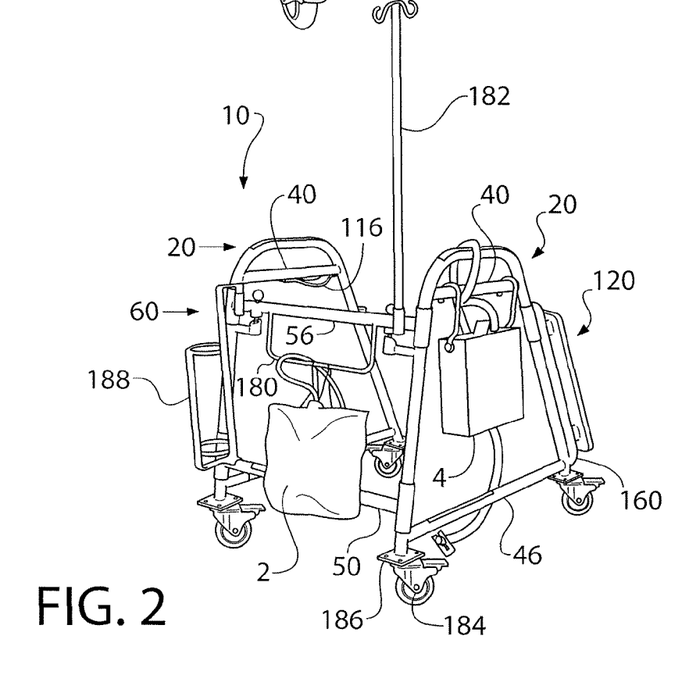
FIG. 2 illustrates another perspective view of a mobility aid apparatus.

Reference is now made, to FIGS. 1-2, wherein the mobility aid apparatus 10 includes a pair of side members, generally designated as 20, which are preferably substantially identical to each other. Each of the pair of side members 20 includes a top rail 22 disposed generally horizontally during use of the apparatus 10, a front elongated leg 24 extending downwardly at a first angle from one end of the top rail 22, a rear elongated leg 32 extending downwardly at a second angle from an opposite end of the top rail 22. The top rail 22, front elongated leg 24 and rear elongated leg 32 are disposed in a same plane and are being positioned generally vertically during use of the mobility aid apparatus 10. A curved connection 39 is contemplated between each end of the top rail 22 and a respective top end of the front and rear elongated legs, 24 and 32 respectively, so as to assist the user in grasping the side member 20, although a sharper connection is also contemplated. Preferably, each side member 20 is provided as a unitary, one-piece member. Preferably, the side members 20 are manufactured from aluminum tubular elements having round cross-section by a welding method, although other metals and other materials, such as plastics, composites and combinations of plastics and metals are also contemplated here.

Although not being essential, it is presently preferred for the apparatus 10 to include a pair of braces 40, each of the pair of braces 40 having each end thereof rigidly secured to a peripheral surfaces of front and rear legs, 24 and 32 respectively, of a respective one of the pair of side members 20 in close proximity to top ends thereof, wherein each of the pair of braces 40 is disposed generally parallel to a top rail 22 of the respective one of the pair of side members 20.

Equally as well, it is presently preferred for the apparatus 10 to include another pair of braces 46, each of the pair of braces 46 having each end thereof rigidly secured to a peripheral surfaces of front and rear legs, 24 and 32 respectively, of the respective one of the pair of side members in close proximity to bottom ends thereof, wherein each of the pair of a braces 46 is disposed generally parallel to each of a top rail 22 and brace 40 of the respective one of the pair of side members 20.

The apparatus 10 also includes a first elongated cross member 50 and a second elongated cross member 56 that are disposed in a generally parallel spaced apart relationship to each other at the front of the apparatus 10.

In accordance with one embodiment of the invention, the apparatus 10 includes means, generally designated as 60, for moving the pair of side members 20 between an operative position, wherein the side members 20 are disposed in a spaced apart generally parallel relationship with each other with the elongated cross members 50 and 56 disposed generally perpendicular to side members 20 and a generally folded position, wherein the side members 20 are juxtaposed in a generally planar relationship with and in close proximity to each other so that the elongated cross members 50 and 56 are disposed at an angle to each side member 20.

Figure 3:
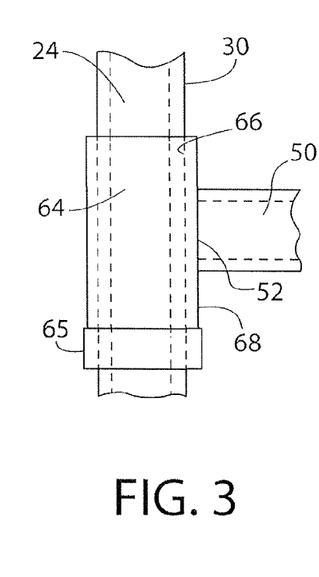
FIG. 3 is a partial front elevation view of the mobility aid apparatus of FIGS. 1-2.
Figure 4:
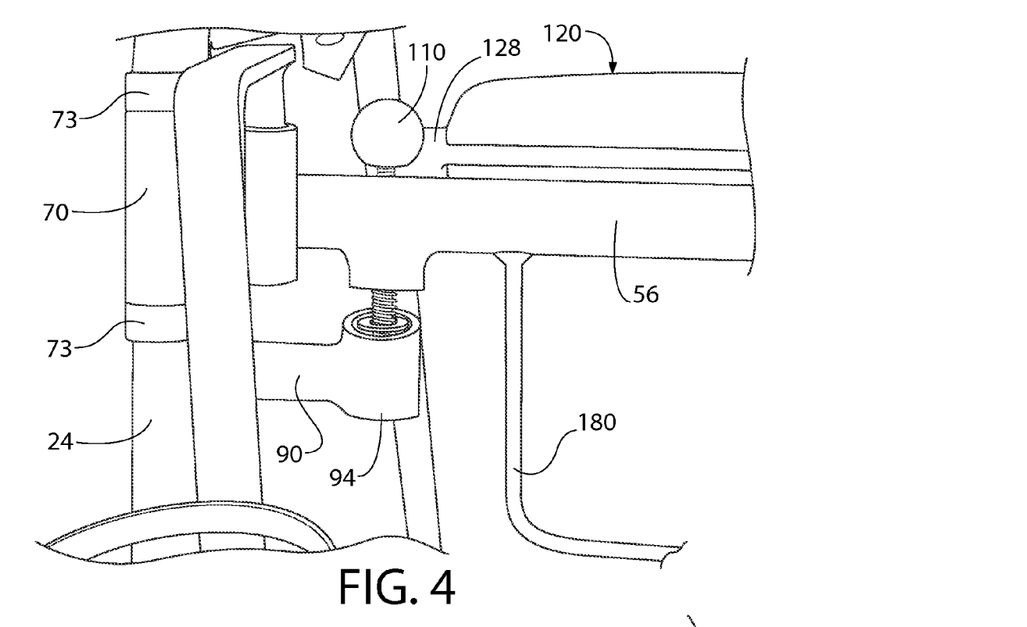
FIG. 4 is another partial front elevation view of the mobility aid apparatus of FIGS. 1-2.
Figure 5:
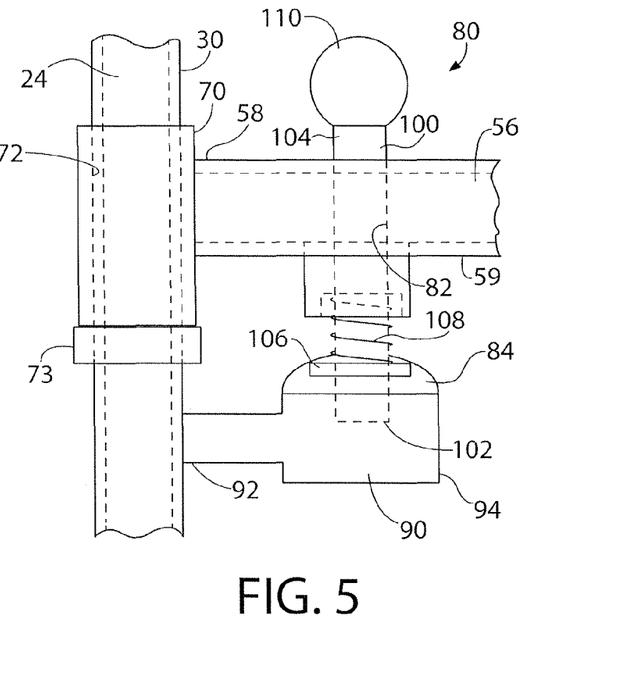
FIG. 5 is detail partial front elevation view of the mobility aid apparatus of FIG. 4.

Now in reference to FIGS. 3-5, the means 60, in accordance with one form, includes means for pivotally connecting each end 52 of the first elongated cross member 50 to a front leg 24 of a respective side member 20 in close proximity to a bottom end 26 of the front leg 24.

The means for pivotally connecting the each end 52 of the first elongated cross member 50 to the front leg 24 of the respective side member 20 in close proximity to the bottom end 26 of the front leg 24 includes a collar 64, best illustrated in FIG. 3, with a hollow interior 66 being so sized and shaped that the collar 64 is mounted for pivoting on a peripheral surface 30 of the front leg 24 and a rigid connection between a peripheral surface 68 of the collar 64 and each end 52 of the first elongated cross member 50. The collar 64 is supported on a member 65 that is rigidly affixed to the front leg 24 and is prevented from moving downwardly. Another member 65 (not shown) can be mounted above the color 64 so as to prevent any movement of the collar 64 along the front leg 24.

The first elongated cross member 50 in combination with a pair of collars 64 define an I-shaped member when the first elongated cross member 50 is positioned vertically.

Means 60 also includes means for pivotally connecting each end 58 of the second elongated cross member 56 to the front leg 24 of the respective side member in close proximity to a top end of the front leg 24. Now in a particular reference to FIG. 5, such means for pivotally connecting the each end 58 of the second elongated cross member 56 to the front leg 24 of the respective side member 20 in close proximity to the top end of the front leg 24 includes another collar 70 with a hollow interior 72 being so sized and shaped that the collar 70 is mounted for pivoting on the peripheral surface 30 of the front leg 24 and another rigid connection between a peripheral surface 74 of the another collar 70 and each end 58 of the second elongated cross member 56. Another collar 70 is supported on a member 73 that is rigidly affixed to the front leg 24. Another member 73 (not shown) can be mounted above the collar 70 so as to prevent any movement of the collar 70 along the front leg 24.

The second elongated cross member 56 in combination with a pair of collars 70 also define an I-shaped member when the second elongated cross member 56 is positioned vertically.

Means 60 includes means, generally designated as 80, for releaseably securing the pair of side members 20 in the operative position in the spaced apart parallel relationship with each other so that the user can stand between the pair of side members 20 and move the apparatus 10 during use thereof.

Now in a more particular reference to FIGS. 4-5, the releaseably securing means 80 includes a pair of arms 90 positioned below the second elongated cross member 56 in a generally parallel relationship therewith during use of the apparatus 10. Each of the pair of arms 90 has a proximal end 92 thereof secured rigidly to the peripheral surface 30 of the front leg 24 of the respective side member 20. Each of the pair of arms 90 extends in a direction toward an opposite one of the pair of front legs 24.

The releaseably securing means 80 further includes a pair of spaced apart apertures 82 formed through a thickness of the second elongated cross member 56 in a generally vertical plane during use of the apparatus 10, a pair of receptacles 84, each of the pair or receptacles 84 disposed on a distal end 94 of a respective arm 90, a pair of elongated pins 100, each of the pair of elongated pins 100 being passed through a respective aperture 82 and having a bottom end 102 thereof operatively received within a respective receptacle 84, so as to at least temporarily secure the pair of arms 90 in the generally parallel relationship with the second elongated cross member 56, and having a top end 104 thereof protruding above a peripheral surface 59 of the second elongated cross member 56. There is also a pair of flanges 106, each of the pair of flanges 106 secured on each of the pair of pins 100 in close proximity to the bottom end 102 thereof. A pair of springs 108 is also provided, each of the pair of springs 108 being caged between a surface of a respective flange 106 and the peripheral surface 59 of the second elongated cross member 56. Finally, there is a pair of gripping members 110, each of the pair of gripping members 110 mounted on the top end 104 of the respective pin 100.

To use the apparatus 10 for assisting the user during walking, the user or a caregiver simply has to assure that the side members 20 are spaced apart and that the arms 90 are generally positioned next to the second elongated cross member 56. Each pin 100 is then pulled upwardly so as to align the respective arm 90 generally parallel to the second elongated cross member 56 and release the pin 100 which allows the bottom end 102 of the pin 100 to engage the respective receptacle 84 due to urging of the spring 108 which is of a compression type.

Figure 6:
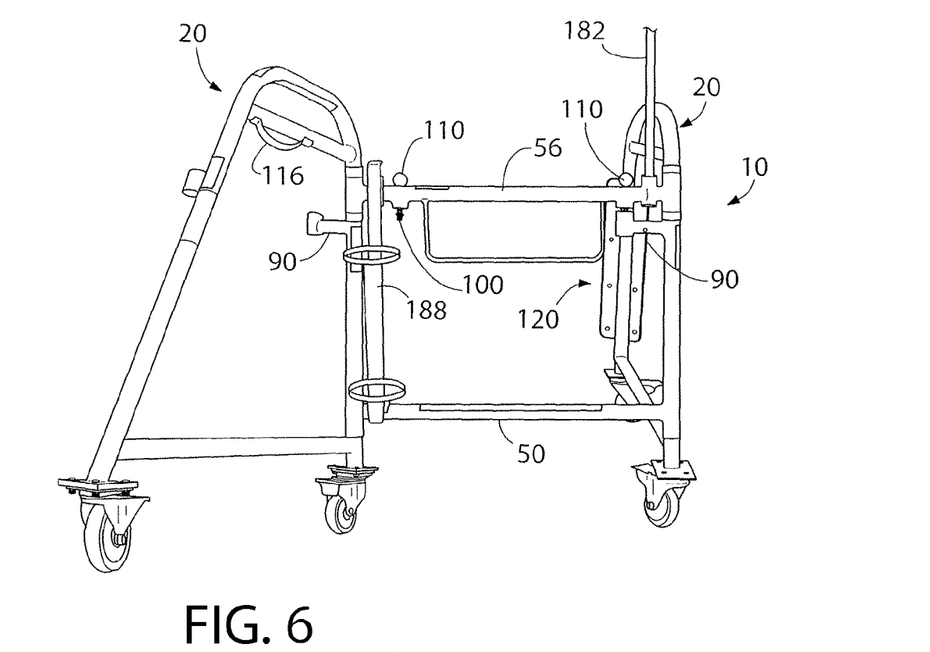
FIG. 6 is a perspective view of the mobility aid apparatus of FIGS. 1-2, particularly illustrating one side frame being in unlatched position.
Figure 7:
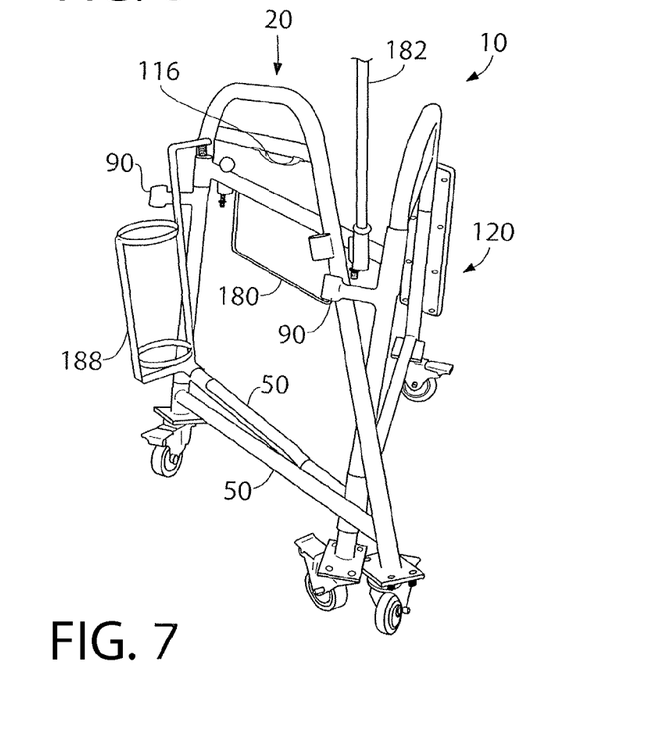
FIG. 7 is a perspective view of the mobility aid apparatus of FIGS. 1-2, particularly illustrating both side frames being in unlatched position for folding the apparatus for storage.

To store the apparatus 10, the pins 100 are pulled upwardly releasing their bottom ends 102 from engagement with the respective receptacles 84 and allowing the side members 20 to pivot about first elongated cross member 50 and about the second elongated cross member 56 toward each other and into the generally folded position, as best shown in FIGS. 6-7, wherein the side members 20 are juxtaposed in a generally planar relationship with and in close proximity to each other so that the elongated cross members 50 and 56 are disposed at an angle to each side member 20.

The apparatus 10 may additionally include a generally flexible strap 116 having one end thereof secured pivotally to one of the pair of side members 20 and having an opposite end thereof detachably attachable to the one or an opposite one of the pair of side members 20. Such strap 116 is employed for at least temporarily securing the side members 20 being moved into the generally folded position by detachably attaching the second end of the strap 116 to the opposite side member 20.

Figure 8:
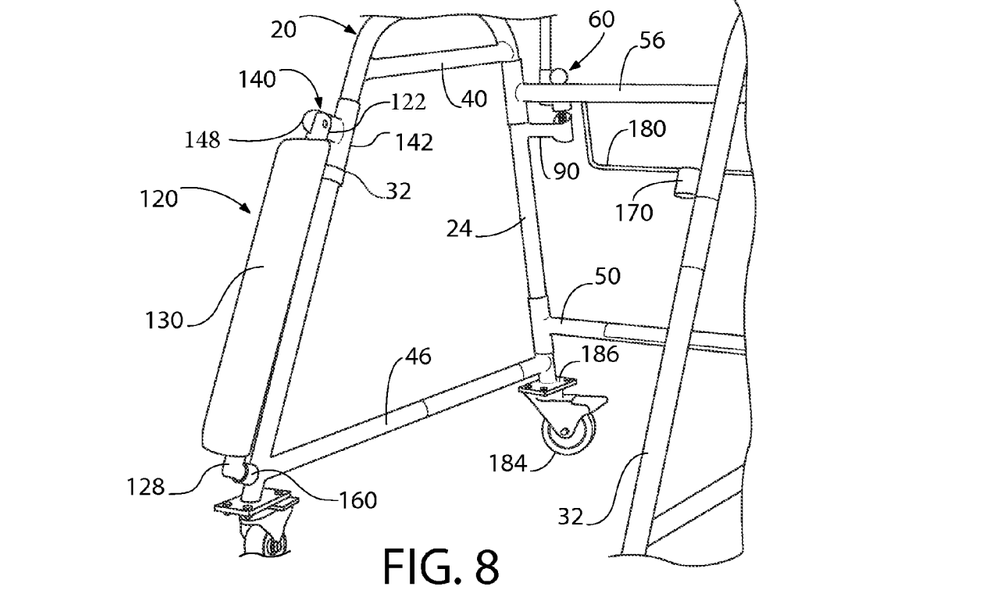
FIG. 8 is a partial rear elevation view of the mobility aid apparatus of FIGS. 1-2.
Figure 9:
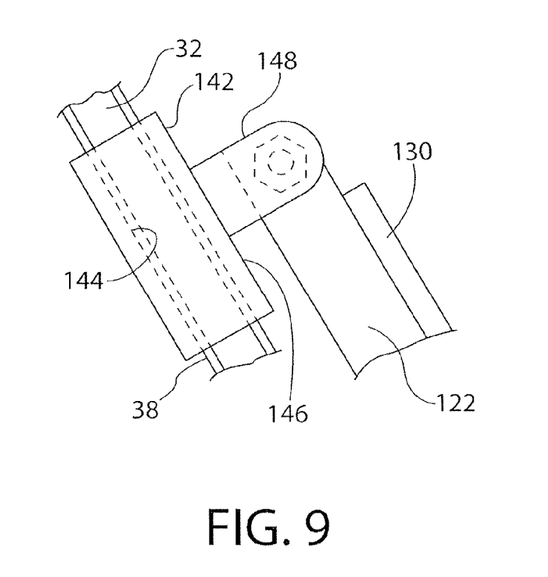
FIG. 9 is a partial side elevation view of the mobility aid apparatus of FIG. 8.
Figure 10:
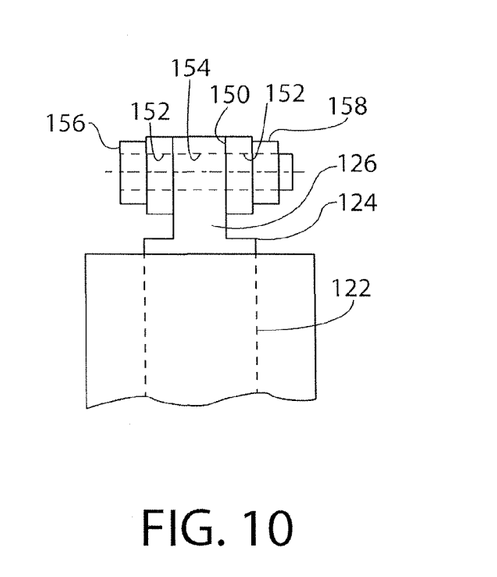
FIG. 10 is front elevation view of the mobility aid apparatus of FIG. 9.

In accordance with another embodiment of the invention, best illustrated in FIGS. 8-10, the apparatus 10 includes a seat, generally designated as 120 and means, generally designated as 140, for moving the seat 120 between a stored position wherein the seat 120 is disposed generally parallel to a rear leg 32 of one of the pair of the side members 20 and a use position wherein the seat 120 is disposed generally horizontally across a space between rear legs 32 of the pair of the side members 20.

The seat 120 includes an elongated support member 122 and an elongated cushioned member 130 securely attached to a peripheral surface of the elongated support member 122, although other shapes of the at least cushioned member 120 are also contemplated here.

The means 140 for moving includes means for pivotally connecting one end of the seat 120 to the rear leg 32 of one of the pair of side members 20, whereby the seat 120 is mounted for pivoting in each of a plane being generally parallel to the rear leg 32 and in a plane being generally perpendicular to the rear leg 32 of the one of the pair of side members 20.

It is presently preferred for such pivot means to include a collar 142 with a hollow interior 144 being so sized and shaped that the collar 140 is mounted for pivoting on a peripheral surface 38 of the rear leg 32. The collar 140 is provided with a seat arm 148 that has a proximal end thereof secured rigidly to the peripheral surface 146 of the collar 140. The distal end of the seat arm 148 is adapted with an end slot or groove 150 that spans the entire thickness of the seat arm 148. There is also a first aperture 152 that is formed through each of a thickness of the distal end of the seat arm 148 and the slot or groove 150. The proximal end 124 of the elongated support member 122 is adapted with a tongue 126 being so shaped and sized that it is received for movement within the slot or groove 150. A second aperture 154 is formed through the proximal end 124 and, more particularly through the thickness of the tongue 126. Finally, a fastener 156 is passed through the first and second apertures, 152 and 154 respectively, being disposed in operative alignment with each other when the tongue 126 is received within the end slot or groove 150. Such fastener may be an elongated pin, a threaded fastener and may further include a threaded nut 158. However, in further reference to FIG. 8, the instant invention also contemplates that the distal end of the seat arm 148 may be provided with a thickness being about half of the thickness of the seat arm 148 and the proximal end 124 of the elongated support member 122 may be also provided with a thickness being about half of the thickness of the elongated support member 122. Such ends are then positioned in a mating relationship with each other and are secured therebetween in a pivotal manner by way the above described of apertures 152 and 154 and fastener 156 that are omitted in FIG. 8.

In order to at least temporarily secure the seat 120 in either position, the apparatus 10 includes a pair of hollow receptacles that may be manufactured from a tubular material or any other suitable hollow shape members. The first hollow receptacle 160 is rigidly mounted on a peripheral surface 38 of the same rear leg 32, having the collar 140 mounted thereon, in close proximity to a bottom end 34 thereof. The first hollow receptacle 160 is so shaped and sized and is so oriented that it receives a distal end 128, which is advantageously bent at about ninety (90) degrees, of the elongated support member 122, whereby the seat 120 is rigidly secured in a semi permanent manner to the afore-mentioned rear leg 32.

The second hollow receptacle 170 is rigidly mounted on a peripheral surface 38 of the opposite rear leg 32 in close proximity to a top end 36 thereof or at a generally the same elevation as the collar 142. The second hollow receptacle 170 is so shaped and sized and is so positioned that it receives the distal end 128 of the elongated support member 122 of the seat 120, whereby the seat 120 is rigidly secured in a semi permanent manner to the rear leg 32 of the opposite one of the pair of side members 20 and whereby the seat 120 is disposed in a generally horizontal plane for supporting the user of the apparatus 10 on the elongated cushioned member 130.

The seat 120 may be provided in combination with or separately from the means 60. In the presently embodiment the seat 120 is provided in combination with the means 60 not only to provide an opportunity for the user to rest but also to stabilize and brace the rear of the apparatus 10 when the seat 120 spans the width of the apparatus 10. However it is contemplated that the seat 120 when positioned in the generally horizontal plane for supporting the user of the apparatus 10 provides the required spacing between the side members 20 so that other means (if any) are used to dispose the elongated cross members 50 and 56 generally perpendicular to side members 20 and retain them in such position during use of the apparatus 10.

When seat 120 is provided for mounting on the rear legs 32, it has been found necessary to configure the apparatus 120 so as to support mandated (user's) weight of about six hundred (600) pounds being positioned at least partially on the seat 120 without tilting the apparatus 10 in a rearward direction. Accordingly, it has been found necessary to provide the second angle of the rear leg 32 so that such rear leg 32 is inclined at about one hundred and twenty (120) degrees to a horizontal surface. Such second angle is also advantageous in positioning the bottom portions of rear legs 32 under the bed or table (not shown) so as to position the front end of the apparatus 10 closer to the user.

The first angle of the front leg 24 may be of any size and, preferably, such first angle is about one hundred (100) degrees.

When the apparatus 10 is not in use, the seat 120 is usually disposed in the stored position, particularly, when the apparatus 10 is in the folded position. This also allows to position the rear legs 32 of the apparatus 10 in proximity to the user and allow the user to enter the space between the side members 20. Then, the seat 120 is pivoted into the use position so as to allow the user to sit and/or brace the rear end of the apparatus 10 for added stability during movement.

In either embodiment, the apparatus 10 may further include means for supporting a plurality of medical devices. By way of an example of FIG. 2, the apparatus 10 includes a generally U-shaped member 180 having each end thereof secured rigidly to the peripheral surface 59 of the second cross member 56. Such generally U-shaped member 180 is advantageous for suspending a Foley bag 2. Additionally, the apparatus 10 may include a vertically disposed rod 182 for supporting, in a hanging manner, an intravenous bag (not shown). Yet additionally, a receptacle 188 may be suspended for housing an oxygen tank (not shown). Yet a cardiac monitor 4 may be suspended from the brace 40.

Finally, four (4) wheels 184 are provided and are securely attached for rotation to bottom ends of the front and rear legs 24 and 32 respectively.

The instant invention also contemplates various alternatives to the means 60.

Figure 11:
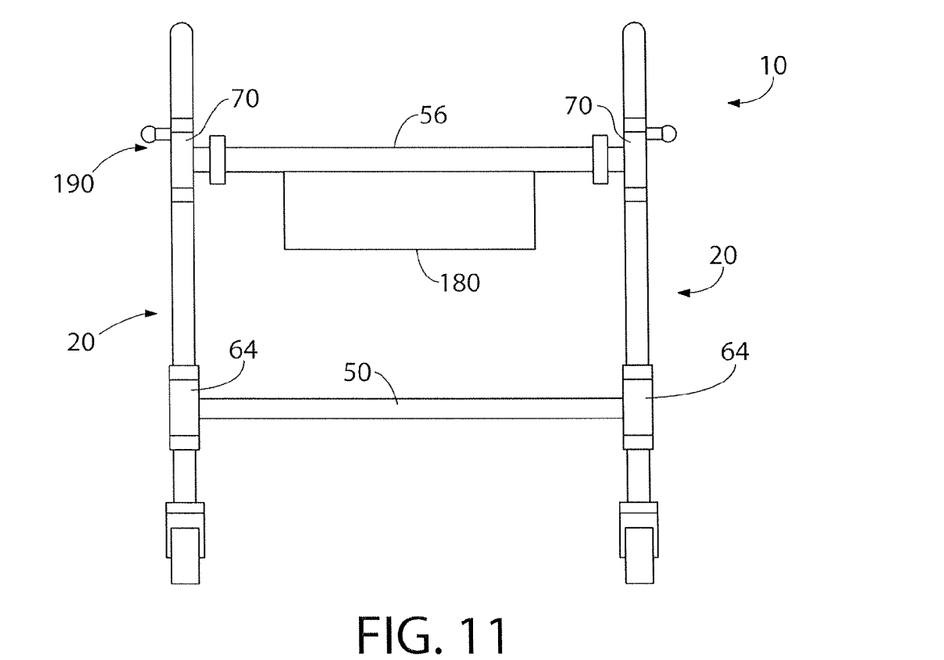
FIG. 11 is a front elevation view of a mobility aid apparatus having latching/latching means constructed in accordance with one alternative embodiment.

By way of an example of FIG. 11, the arms 90 may be disposed in the plane of the side member 20, for example being disposed below and generally parallel to the braces 40 and a latch 190 is operable from each side of the apparatus 10.

Figure 12:
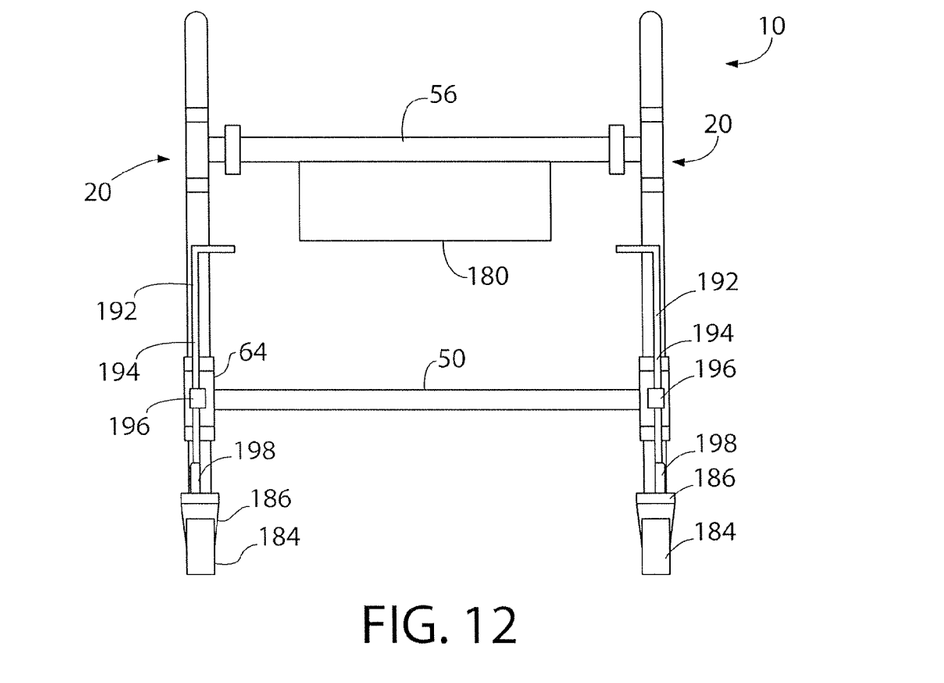
FIG. 12 is a front elevation view of a mobility aid apparatus having latching/latching means constructed in accordance with another alternative embodiment.

By way of another example of FIG. 12, the apparatus 10 may include an L-shaped member 192 having a longer leg 194 thereof being passed though a guide sleeve 196 attached to the peripheral surface 68 of the collar 64. The distal end of the longer leg 194 is operatively received within a receptacle 198 rigidly secured to the plate 186 of the front wheel 184.

The apparatus 10 may be manufactured to support lighter weight and may be made in different widths so as to operate in tight areas.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

I claim:

1. A mobility aid apparatus comprising:
   (a) a pair of unitary one-piece side members disposed in a spaced apart relationship with each other, each of said pair of side members manufactured from a tubular material and including:
      i. a top rail disposed generally horizontally during use of said apparatus,
      ii. a front elongated leg extending downwardly at a first angle from one end of said top rail,
      iii. a rear elongated leg extending downwardly at a second angle from an opposite end of said top rail,
      iv. a curved connection between each end of said top rail and a respective top end of said front and rear elongated legs, and
      v. wherein said top, front and rear legs are disposed in a same plane;
   (b) a pair of first braces, each of said pair of first braces having each end thereof rigidly secured to a peripheral surface of front and rear legs of a respective one of said pair of side members in close proximity to top ends thereof, wherein said each of said pair of first braces is disposed generally parallel to a top rail of said respective one of said pair of side members;
   (c) a pair of second braces, each of said pair of second braces having each end thereof rigidly secured to said peripheral surface of said front and rear legs of said respective one of said pair of side members in close proximity to bottom ends thereof, wherein said each of said pair of second braces is disposed generally parallel to said top rail of said respective one of said pair of side members;
   (d) a first elongated cross member;
   (e) first means for pivotally connecting each end of said first elongated cross member to a front leg of a respective side member in close proximity to a bottom end of said front leg, said first means including a collar with a hollow interior being so sized and shaped that said collar is mounted for pivoting on a peripheral surface of said front leg and a rigid connection between a peripheral surface of said collar and said each end of said first elongated cross member;
   (f) a second elongated cross member;
   (g) second means for pivotally connecting each end of said second elongated cross member to said front leg of said respective side member in close proximity to a top end of said front leg, said second means including another collar with a hollow interior being so sized and shaped that said another collar is mounted for pivoting on said peripheral surface of said front leg and another rigid connection between a peripheral surface of said another collar and said each end of said second elongated cross member;

(h) a pair of arms positioned below said second elongated cross member in a generally parallel relationship therewith during use of said apparatus, each of said pair of arms having a proximal end thereof secured rigidly to a peripheral surface of said front leg of said respective side member, said each of said pair of arms extending in a direction toward an opposite one of said pair of front legs;

(i) means for releaseably securing said pair of side members in a spaced apart generally parallel relationship with each other so that a user can stand between said pair of side members and move said apparatus during use thereof, said releaseably securing means including:
   i. a pair of spaced apart apertures formed through a thickness of said second elongated cross member in a generally vertical plane during use of said apparatus,
   ii. a pair of receptacles, each of said pair or receptacles disposed on a distal end of a respective arm,
   iii. a pair of elongated pins, each of said pair of elongated pins passed through a respective aperture and having a bottom end thereof operatively received within a respective receptacle so as to at least temporarily secure said pair of arms in said generally parallel relationship,
   iv. a pair of flanges, each of said pair of flanges secured on each of said pair of pins in close proximity to said bottom end thereof,
   v. a pair of springs, each of said pair of springs caged between a surface of a respective flange and a peripheral surface of said second elongated cross member, and
   vi. a pair of gripping members, each of said pair of gripping members mounted on a top end of a respective pin;

(j) a seat including an elongated support member and an elongated cushioned member securely attached to a peripheral surface of said elongated support member;

(k) means for pivotally connecting one end of said elongated support member to a rear leg of one of said pair of side members, whereby said seat is mounted for pivoting in each of a plane being generally parallel to said rear leg of said one of said pair of side members and in a plane being generally perpendicular to said rear leg of said one of said pair of side members, said pivoting means including:
   i. yet another collar with a hollow interior being so sized and shaped that said yet another collar is mounted for pivoting on a peripheral surface of said rear leg,
   ii. a seat arm having a proximal end thereof rigidly secured on a peripheral surface of said yet another collar,
   iii. a slot formed through a distal end of said seat arm,
   iv. a first aperture formed through each of a thickness of said distal end of said seat arm and said slot,
   v. a tongue formed on one end of said elongated support member,
   vi. a second aperture formed through said tongue, and
   vii. a fastener passed through said first and second apertures being disposed in operative alignment with each other when said tongue is received within said end slot;

(l) a first receptacle rigidly mounted on a peripheral surface of said rear leg of said one of said pair of side members in close proximity to a bottom end thereof, said first receptacle is so shaped and sized that it receives an opposite end of said elongated support member, whereby said seat is rigidly secured in a semi permanent manner to said rear leg of said one of said pair of side members;

(m) a second receptacle rigidly mounted on a peripheral surface of a rear leg of an opposite one of said pair of side members in close proximity to a top end thereof, said second receptacle is so shaped and sized that it receives said opposite end of said elongated support member, whereby said seat is rigidly secured in a semi permanent manner to said rear leg of said opposite one of said pair of side members and whereby said seat is disposed in a generally horizontal plane for supporting the user of said apparatus on said elongated cushioned member;

(n) a generally U-shaped elongated member having each end thereof secured rigidly to a peripheral surface of said first cross member;

(o) a generally flexible strap having one end thereof pivotally secured to a peripheral surface of one of said pair of first braces and having an opposite end thereof detachably attachable to a peripheral surface of another one of said pair of first braces; and (p) a quartet of wheels, each of said quartet of wheel attached for rotation to a distal end of each of said front and rear leg of said pair of side members.

2. A mobility aid apparatus comprising:
(a) a pair of side members disposed in a spaced apart relationship with each other, each of said pair of side members including:
   i. a top rail disposed generally horizontally during use of said apparatus,
   ii. a front elongated leg extending downwardly at a first angle from one end of said top rail,
   iii. a rear elongated leg extending downwardly at a second angle from an opposite end of said top rail, and
   iv. wherein said top, front and rear legs are disposed in a same plane;

(b) a pair of braces, each of said pair of braces having each end thereof rigidly secured to a peripheral surface of said front and rear legs of a respective one of said pair of side members in a close proximity to bottom ends thereof;

(c) first and second elongated cross members having each end thereof secured to a peripheral surface of a respective front leg;

(d) a seat including an elongated support member and an elongated cushioned member securely attached to a peripheral surface of said elongated support member;

(e) a pivotal connection between one end of said elongated support member to a rear leg of one of said pair of side members, whereby said seat is mounted for pivoting in each of a plane being generally parallel to said rear leg of said one of said pair of side members and in a plane being generally perpendicular to said rear leg of said one of said pair of side members, said pivotal connection including:
   i. a collar with a hollow interior being so sized and shaped that said a collar is mounted for pivoting on a peripheral surface of said rear leg,
   ii. a seat arm having a proximal end thereof rigidly secured on a peripheral surface of said yet another collar,
   iii. a slot formed through a distal end of said seat arm, iv. a first aperture formed through each of a thickness of said distal end of said seat arm and said slot,
v. a tongue formed on one end of said elongated support member,
vi. a second aperture formed through said tongue, and
vii. a fastener passed through said first and second apertures being disposed in operative alignment with each other when said tongue is received within said end slot;
(f) a first receptacle rigidly mounted on a peripheral surface of said rear leg of said one of said pair of side members in close proximity to a bottom end thereof, said first receptacle is so shaped and sized that it receives an opposite end of said elongated support member, whereby said seat is rigidly secured in a semi permanent manner to said rear leg of said one of said pair of side members;
(g) a second receptacle rigidly mounted on a peripheral surface of a rear leg of an opposite one of said pair of side members in close proximity to a top end thereof, said second receptacle is so shaped and sized that it receives said opposite end of said elongated support member, whereby said seat is rigidly secured in a semi permanent manner to said rear leg of said opposite one of said pair of side members and whereby said seat is disposed in a generally horizontal plane for supporting the user of said apparatus on said elongated cushioned member; and
(h) a quartet of wheels, each of said quartet of wheel attached for rotation to a distal end of each of said front and rear leg of said pair of side members.

3. The apparatus of claim 2, further including a pair of another braces, each of said pair of another braces having each end thereof rigidly secured to said peripheral surface of said front and rear legs of said respective one of said pair of side members in a close proximity to top ends thereof, wherein said each of said pair of another braces is disposed generally parallel to a top rail of said respective one of said pair of side members.

4. The apparatus of claim 2, further including a cross member connected to front legs of said pair of side members and a generally U-shaped elongated member having each end thereof secured rigidly to a peripheral surface of said cross member.

5. The apparatus of claim 2, further including a generally flexible strap having one end thereof secured pivotally to one of said pair of side members and having an opposite end thereof detachably attachable to said one or an opposite one of said pair of side members.

6. The apparatus of claim 2, further comprising:
(a) a first pivotal connection between said each end of said first elongated cross member and said front leg of said respective side member in a close proximity to said bottom end of said front leg, said first pivotal connection including another collar with a hollow interior being so sized and shaped that said another collar is mounted for pivoting on a peripheral surface of said front leg and a rigid connection between a peripheral surface of said another collar and said each end of said first elongated cross member;
(b) a second pivotal connection between said each end of said second elongated cross member and said front leg of said respective side member in a close proximity to said top end of said front leg, said second pivotal connection including yet another collar with a hollow interior being so sized and shaped that said yet another collar is mounted for pivoting on said peripheral surface of said front leg and another rigid connection between a peripheral surface of said yet another collar and said each end of said second elongated cross member
(c) whereby said pair of side members are movable between an operative position, wherein said side members are disposed in a spaced apart generally parallel relationship with each other and a generally folded position, wherein said side members are generally juxtaposed in a generally planar relationship with and in close proximity to each other;
(d) a pair of arms positioned below said second elongated cross member in a generally parallel relationship therewith during use of said apparatus, each of said pair of arms having a proximal end thereof secured rigidly to a peripheral surface of said front leg of said respective side member, said each of said pair of arms extending in a direction toward an opposite one of said pair of front legs;
(e) a pair of spaced apart apertures formed through a thickness of said second elongated cross member in a generally vertical plane during use of said apparatus;
(f) a pair of receptacles, each of said pair or receptacles disposed on a distal end of a respective arm;
(g) a pair of elongated pins, each of said pair of elongated pins passed through a respective aperture and having a bottom end thereof operatively received within a respective receptacle of said pair of receptacles so as to at least temporarily secure said pair of arms in said generally parallel relationship and having a top end thereof protruding above a peripheral surface of said second elongated cross member;
(h) a pair of flanges, each of said pair of flanges secured on each of said pair of pins in close proximity to said bottom end thereof;
(i) a pair of springs, each of said pair of springs caged between a surface of a respective flange and said peripheral surface of said second elongated cross member; and
(j) a pair of gripping members, each of said pair of gripping members mounted on a top end of a respective pin.

7. The apparatus of claim 2, further comprising:
(a) a means for pivotally connecting each end of said first elongated cross member to said front leg of said respective side member in close proximity to a bottom end of said front leg;
(b) a means for pivotally connecting each end of said second elongated cross member to said front leg of said respective side member in close proximity to a top end of said front leg;
(c) whereby said pair of side members are movable between an operative position, wherein said side members are disposed in a spaced apart generally parallel relationship with each other and a generally folded position, wherein said side members are generally juxtaposed in a generally planar relationship with and in close proximity to each other;
(d) a pair of arms positioned below said second elongated cross member in a generally parallel relationship therewith during use of said apparatus, each of said pair of arms having a proximal end thereof secured rigidly to a peripheral surface of said front leg of said respective side member, said each of said pair of arms extending in a direction toward an opposite one of said pair of front legs; and
(e) a means for releaseably securing said pair of side members in said operative position so that a user can stand between said pair of side members and move said apparatus during use thereof.

8. The apparatus of claim 7, wherein said means for pivotally connecting said each end of said first elongated cross member to said front leg of said respective side member in close proximity to said bottom end of said front leg includes another collar with a hollow interior being so sized and shaped that said another collar is mounted for pivoting on a peripheral surface of said front leg and a rigid connection between a peripheral surface of said another collar and said each end of said first elongated cross member.

9. The apparatus of claim 7, wherein said means for pivotally connecting said each end of said second elongated cross member to said front leg of said respective side member in close proximity to said top end of said front leg includes another collar with a hollow interior being so sized and shaped that said another collar is mounted for pivoting on said peripheral surface of said front leg and another rigid connection between a peripheral surface of said another collar and said each end of said second elongated cross member.

10. The apparatus of claim 7, wherein said releaseably securing means includes:

(a) a pair of spaced apart apertures formed through a thickness of said second elongated cross member in a generally vertical plane during use of said apparatus;
(b) a pair of receptacles, each of said pair or receptacles disposed on a distal end of a respective arm;
(c) a pair of elongated pins, each of said pair of elongated pins passed through a respective aperture and having a bottom end thereof operatively received within a respective receptacle of said pair of receptacles so as to at least temporarily secure said pair of arms in said generally parallel relationship and having a top end thereof protruding above a peripheral surface of said second elongated cross member;
(d) a pair of flanges, each of said pair of flanges secured on each of said pair of pins in close proximity to said bottom end thereof;
(e) a pair of springs, each of said pair of springs caged between a surface of a respective flange and said peripheral surface of said second elongated cross member; and
(f) a pair of gripping members, each of said pair of gripping members mounted on a top end of a respective pin.

* * * * *